(12) United States Patent
Funderburk et al.

(10) Patent No.: US 6,520,938 B1
(45) Date of Patent: Feb. 18, 2003

(54) MEDICATION INFUSION SET

(75) Inventors: Jeffery V. Funderburk, Granada Hills, CA (US); Leif N. Bowman, Westminster, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 09/623,287
(22) PCT Filed: Mar. 3, 1999
(86) PCT No.: PCT/US99/04757
§ 371 (c)(1), (2), (4) Date: Aug. 31, 2000
(87) PCT Pub. No.: WO99/44655
PCT Pub. Date: Sep. 10, 1999

Related U.S. Application Data

(63) Continuation of application No. 09/034,626, filed on Mar. 4, 1998, now Pat. No. 6,056,718.

(51) Int. Cl.[7] .............................................. A61M 5/178
(52) U.S. Cl. ........................... 604/164.08; 604/164.04; 604/178; 604/244; 604/256; 604/162
(58) Field of Search .............................. 604/93.01, 161, 604/164.01, 164.04, 164.08, 167.06, 174, 175, 244, 245, 256, 263, 264, 272, 162

(56) References Cited

U.S. PATENT DOCUMENTS 3,973,565 A 8/1976 Steer (List continued on next page.)

FOREIGN PATENT DOCUMENTS

| DE | 2950309 | 2/1995 | .......... A61M/5/158 |
| FR | 2242114 | 8/1973 | ............ A61M/5/32 |
| WO | 9858693 | 12/1998 | ............ A61M/5/00 |

OTHER PUBLICATIONS

Betty Brackenridge, MS,RD,CDE; Janet Bryant, RN, CETN; Ruth Farkas–Hirsch, MS,RN,CDE; Madelein Fernandez, LPN; Paul Schickling, RPH,CDE; Leigh Steed, RN,CDE; & Suzanne Strowig, MSN,RN,CDE, "Tape Tips and Other Infusion Site Information", MiniMed Technologies Inc. (1995); pp. 3–11.

International Search Report for Internatonal Application No. PCT/US99/04757.

*Primary Examiner*—Brian L. Casler
*Assistant Examiner*—Jeremy Thissell
(74) *Attorney, Agent, or Firm*—Medtronic MiniMed, Inc.

(57) ABSTRACT

An improved medication infusion set is provided of the type having a soft cannula for subcutaneous delivery of a selected medication to a patient. The infusion set comprises a cannula housing having a soft cannula protruding therefrom and a self-sealing septum mounted at an upstream end of the cannula. The cannula housing is initially assembled with an insertion hub having an elongated insertion needle extending through the septum and cannula for transcutaneously placing the cannula followed by separation of the insertion hub from the cannula housing. An infusion hub is then assembled with the cannula housing and includes a short infusion needle for coupling the cannula with the selected medication supplied from a source via a length of infusion tubing. The infusion hub includes a protective shroud plate protruding beyond a tip end of the infusion needle to minimize risk of patient contact therewith, and adapted for slide-fit reception into a matingly shaped slot formed in the cannula housing to insure a one-way and high strength interconnection between the cannula housing and infusion hub. Releasable latch members interlock the infusion hub with the cannula housing in a manner permitting periodic separation when desired.

13 Claims, 7 Drawing Sheets

U.S. PATENT DOCUMENTS

| | | |
|---|---|---|
| 4,245,635 A | 1/1981 | Kontos |
| 4,562,751 A | 1/1986 | Nason et al. |
| 4,573,994 A | 3/1986 | Fischell et al. |
| 4,678,408 A | 7/1987 | Nason et al. |
| 4,685,903 A | 8/1987 | Cable et al. |
| 4,755,173 A | 7/1988 | Konopka et al. |
| 4,880,412 A | 11/1989 | Weiss |
| 4,950,252 A | 8/1990 | Luther et al. |
| 5,080,653 A | 1/1992 | Voss et al. |
| 5,097,122 A | 3/1992 | Colman et al. |
| 5,176,662 A | 1/1993 | Bartholomew et al. |
| 5,201,717 A | 4/1993 | Wyatt et al. |
| 5,257,980 A | 11/1993 | Van Antwerp et al. |
| 5,299,571 A | 4/1994 | Mastrototaro |
| 5,346,479 A | 9/1994 | Schneider |
| 5,356,389 A | 10/1994 | Willing |
| 5,390,671 A | 2/1995 | Lord et al. |
| 5,391,250 A | 2/1995 | Cheney, II et al. |
| 5,423,775 A | 6/1995 | Cannon |
| 5,482,473 A | 1/1996 | Lord et al. |
| 5,522,803 A | 6/1996 | Teissen-Simony |
| 5,568,806 A | 10/1996 | Cheney, II et al. |
| 5,584,813 A | 12/1996 | Livingston et al. |
| 5,647,853 A | 7/1997 | Feldmann et al. |
| 5,728,071 A | 3/1998 | Watson et al. |
| 5,762,632 A | 6/1998 | Whisson |

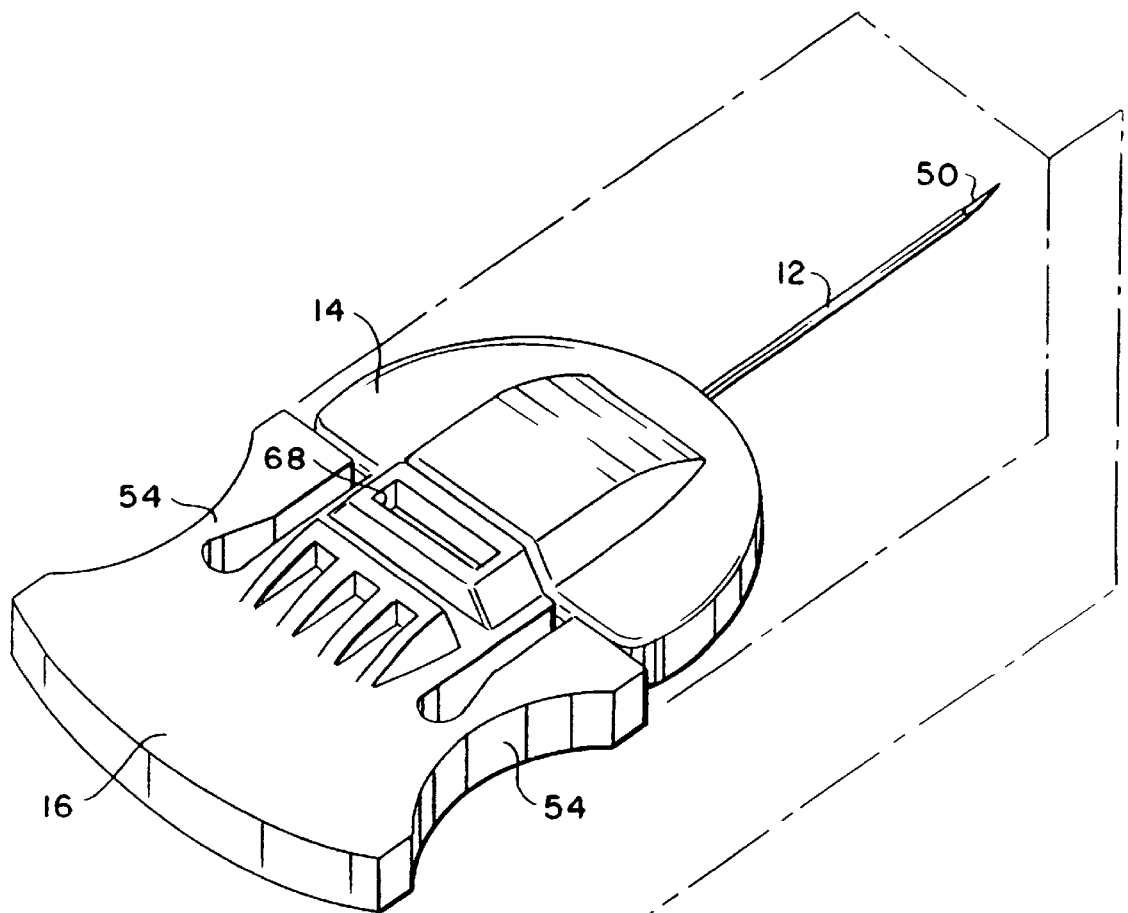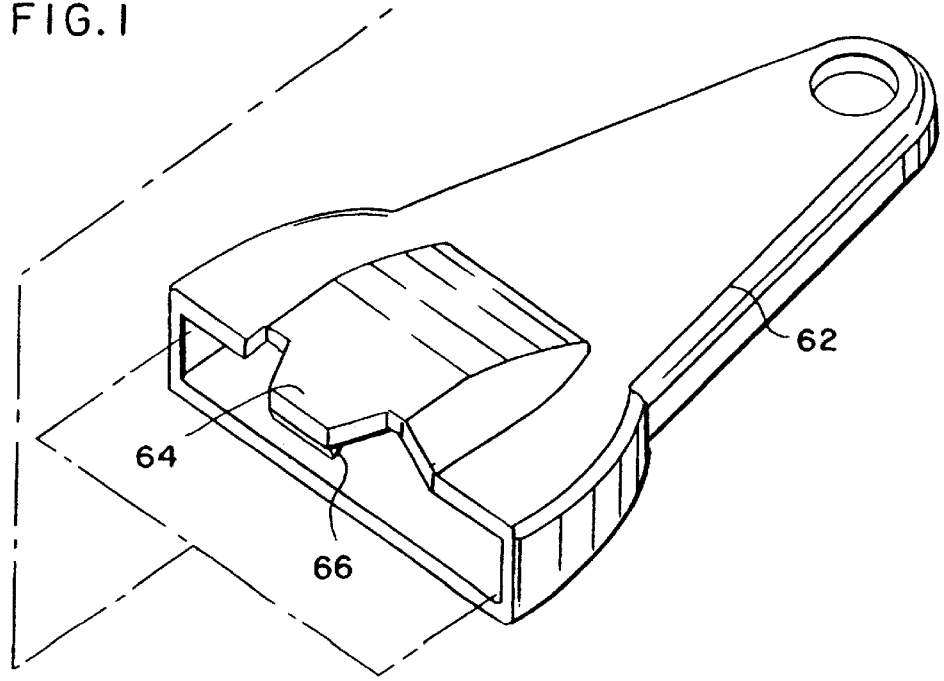
FIG. 1

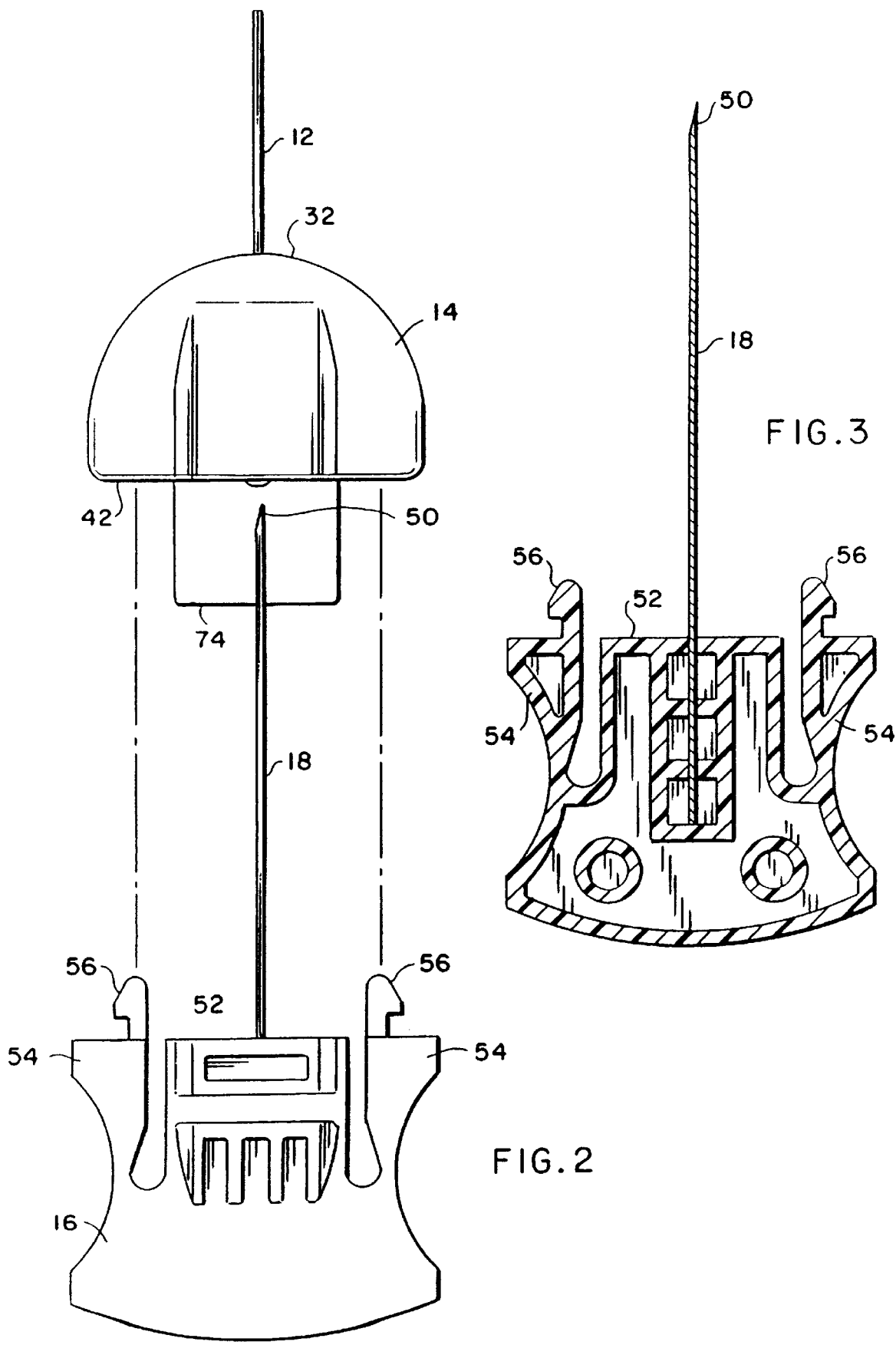

MEDICATION INFUSION SET

This application is a national stage entry of PCT/US99/04757 filed Mar. 3, 1999, which is a continuation of U.S. Ser. No. 09/034,626 filed Mar. 4, 1998 now U.S. Pat. No. 6,056,718.

BACKGROUND OF THE INVENTION

This invention relates generally to devices and methods for delivering a selected medication or other therapeutic fluid to a patient at a subcutaneous infusion site. More particularly, this invention relates to an improved medication infusion set of the type having a soft or flexible cannula adapted for subcutaneous placement, in combination with an infusion needle associated with a protective shroud plate to minimize risk of patient contact therewith while providing a high strength and unidirectional releasible coupling with the cannula.

Medication injection or infusion sets are generally well known in the art, to include a relatively soft and flexible cannula providing a transcutaneous pathway through which a selected medication or other therapeutic fluid can be administered to a patient at a selected subcutaneous site. In a common form, the soft cannula is carried by a compact housing to include a resilient self-sealing septum mounted at an upstream end of the cannula. This cannula housing is initially assembled with an insertion needle extending through the septum and cannula, wherein the insertion needle is manipulated to pierce the patient's skin to place the cannula transcutaneously, followed by withdrawal of the insertion needle to leave the soft cannula in place on the patient. The selected medication is then coupled to the cannula, typically by means of a length of infusion tubing connected to a medication source, to deliver the medication through the cannula to the patient. In one configuration, the infusion tubing is connected to the cannula housing at a location downstream from the septum as shown, for example, in U.S. Pat. Nos. 4,755,173; 5,176,662; and 5,257,980. In another arrangement, the infusion tubing is coupled to the cannula housing by means of an infusion needle passed through the septum as shown, for example, in U.S. Pat. No. 5,522,803.

Subcutaneous infusion sets of the above-described type are used extensively to administer medication to a patient over an extended period of time. For example, such infusion sets are used with medication infusion pumps of the type described in U.S. Pat. Nos. 4,562,751; 4,685,903; 5,080,653; and 5,097,122 for delivering a long-term medication such as insulin in a continuous or programmable dosage to the patient. With such medication delivery systems, however, it is known that the medication source must be periodically disconnected from the cannula. For example, it has been recognized that the infusion set should be replaced every few days, whereby it is necessary for the patient to uncouple the medication source from an in situ cannula upon removal thereof from the patient, and to recouple the infusion tubing with a second, newly placed cannula. In addition, some patients may briefly disconnect the medication source and related infusion tubing from the cannula to facilitate certain activities, such as swimming or bathing, or participation in certain athletic activities, etc.

In this regard, an optimal medication infusion set is adapted for low profile and in obtrusive placement on the patient, while permitting quick and safe periodic disconnection from and reconnection to the medication source. To this end, use of an infusion needle adapted for coupling through the self-sealing septum provides a quick and easy structure for connecting and disconnecting the medication source from the cannula, but also subjects the patient to undesirable needle sticks from exposure to the infusion needle. Moreover, this arrangement requires a strong and reliable mechanical interlock between the cannula housing and the infusion needle to insure consistent and proper interengagement without inadvertent component separation, while permitting quick and easy and repeated disconnection when desired. All of these features are desirably provided in an infusion set constructed from relatively simple and preferably disposable components which can be manufactured in a cost-efficient manner from medical grade plastic or the like.

The present invention provides an improved medication infusion set designed to meet these features and advantages, by including an infusion needle associated with a protective shroud plate. The shroud plate closely overlies and substantially encases the infusion needle in a manner minimizing risk of patient contact therewith, while additionally providing a strong guide structure for keyed or one-way interconnection with a cannula housing.

SUMMARY OF THE INVENTION

In accordance with the invention, an improved medication infusion set is provided for use in delivering medication through a soft cannula to a selected subcutaneous infusion site on a patient. The soft cannula is supported by a compact and low profile cannula housing which includes a self-sealing septum disposed at a proximal or upstream end of the cannula. An infusion hub is provided with latch means for releasible assembly with the cannula housing, and includes a short infusion needle coupled via infusion tubing or the like to a source of the selected medication. The infusion hub includes a protective shroud plate which closely overlies and substantially encases the infusion needle to reduce risk of inadvertent patient contact therewith. The protective shroud plate is configured for unidirectional or one-way reception into a matingly shaped slot formed in the cannula housing upon assembly of the components to provide a high strength connection.

In the preferred form on the invention, the cannula housing comprises a compact plastic molding defining an internal bore for seated reception of a proximal end of the soft cannula. A generally cylindrical needle guide is also seated within the cannula housing and has a downstream end press-fitted into the cannula proximal end. The needle guide defines a flared upstream end, and a ball-shaped resilient and self-sealing septum is retained therein by a retainer clip adapted for snap-fit mounting onto the cannula housing.

The cannula housing is initially assembled with an insertion hub which may also be formed from a molded plastic and includes at least one and preferably a pair of resilient latch arms for snap-fit reception into aligned latch ports formed in a proximal face of the cannula housing. The insertion hub carries an elongated insertion needle passed through the septum and needle guide, and further through the soft cannula terminating in a pointed tip end disposed a short distance beyond the distal or downstream end of the cannula. The insertion needle is utilized to pierce the patient's skin at a selected medication infusion site, to transcutaneously place the soft cannula, after which the insertion hub is separated from the cannula housing to withdraw the insertion needle from the cannula.

The infusion hub also comprises a low profile component of molded plastic or the like and carries the infusion needle in flow communication with the source of the selected medication, typically via a length of infusion tubing. The infusion needle protrudes from a distal face of the infusion hub in close association with the protective shroud plate which protrudes at least slightly beyond the tip end of the infusion needle. In a preferred form, the shroud plate comprises a multifaceted and preferably three-sided structure enclosing the infusion needle on three sides to substantially prevent patient contact and accidental needle sticks. The shroud plate is configured for slide-fit reception into a matingly shaped slot formed in the proximal face of the cannula housing, with a one-way fit, for accurate guided reception of the infusion needle through the septum to extend partially into the needle guide. At least one and preferably a pair of resilient latch arms on the infusion hub are provided for snap-fit reception into the latch ports on the cannula housing to releasibly interlock the components.

In use, the infusion hub is securely coupled with the cannula housing with a high strength interconnection resistant to bending or twisting forces that could otherwise contribute to inadvertent component separation. However, the infusion hub can be quickly and easily disconnected from the cannula housing when desired, for example, when the cannula is replaced or during patient activities requiring temporary disconnection of the medication source. The infusion hub is adapted for quick and easy reconnection to the existing or to a replacement cannula housing, with a simple one-way snap-fit connection, and with the infusion needle substantially concealed from patient contact at all times.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is an exploded perspective view illustrating a medication infusion set formed in accordance with the novel features of the invention, to include a cannula housing assembled with an insertion hub, shown in exploded relation with a needle guard;

FIG. 2 is a top plan view showing the cannula housing and insertion hub in exploded relation;

FIG. 3 is a horizontal sectional view of the insertion hub;

DETAILED DESCRIPTION OF THE PREFERRED EMBODIMENT

Figure 4:
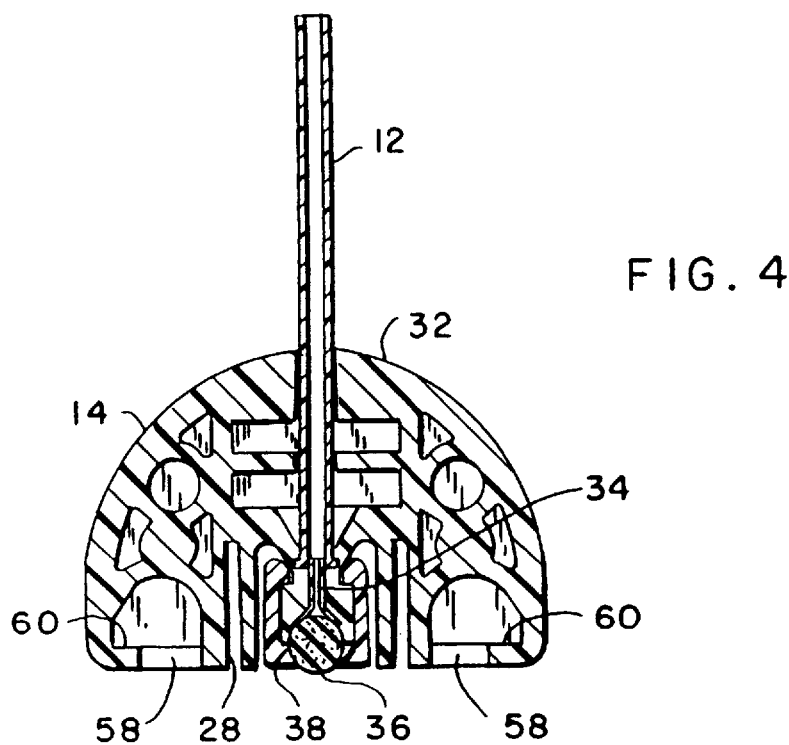
FIG. 4 is a horizontal sectional view of the cannula housing.

As shown in the exemplary drawings, an improved infusion set is provided for use in administering a selected medication to a patient at a selected subcutaneous infusion site. The infusion set comprises a soft and flexible cannula 12 carried by a compact and low profile cannula housing 14. An inserter hub 16 including an insertion needle 18 is initially assembled with the cannula housing 14 for transcutaneously placing the cannula, as viewed in FIGS. 1–6 and 11. Thereafter, an infusion hub 20 including an infusion needle 22 coupled to a source of a selected medication via a length of infusion tubing 24 is assembled with the cannula housing 14 for delivering the medication to the patient, as viewed in FIGS. 7–10. The infusion hub 20 includes a protective shroud plate 26 closely overlying the infusion needle 22 to prevent undesirable needle sticks, wherein the shroud plate 26 slide-fits into a mating slot 28 formed in the cannula housing 14 to provide a one-way and high strength interconnection of the components.

The medication infusion set of the present invention is particularly suited for delivering medication to a patient on a continuous or programmable basis over an extended period of time, such as, for example, the administration of insulin to a diabetic patient by means of a programmable infusion pump of the type described in U.S. Pat. Nos. 4,562,751; 4,685,903; 5,080,653; and 5,097,122. The infusion set comprises a compact, low profile and economical assembly of components adapted for quick and easy transcutaneous placement of the soft cannula 12 at the selected infusion site, followed by quick and easy coupling of the cannula with the selected medication source. The infusion hub 20 and the cannula housing 14 are constructed for facilitated and repeated interconnection with a unidirectional or one-way fit while minimizing risk of patient contact with the infusion needle 18, and further to provide a high strength attachment which is resistant to inadvertent separation in response to bending, twisting, and tension forces. In addition, the infusion hub 20 and associated infusion needle 18 can be disconnected quickly and easily from the cannula housing 14 by the patient as may be required or desired, for example, when replacing the cannula typically at intervals of several days, or when the patient participates in athletic or other activities such as swimming or bathing wherein temporary disconnection of the infusion pump is warranted. Importantly, the infusion hub 20 can be reconnected rapidly and safely by the patient to the existing or to a replacement cannula housing to provide a strong and reliable component interface.

Figure 5:
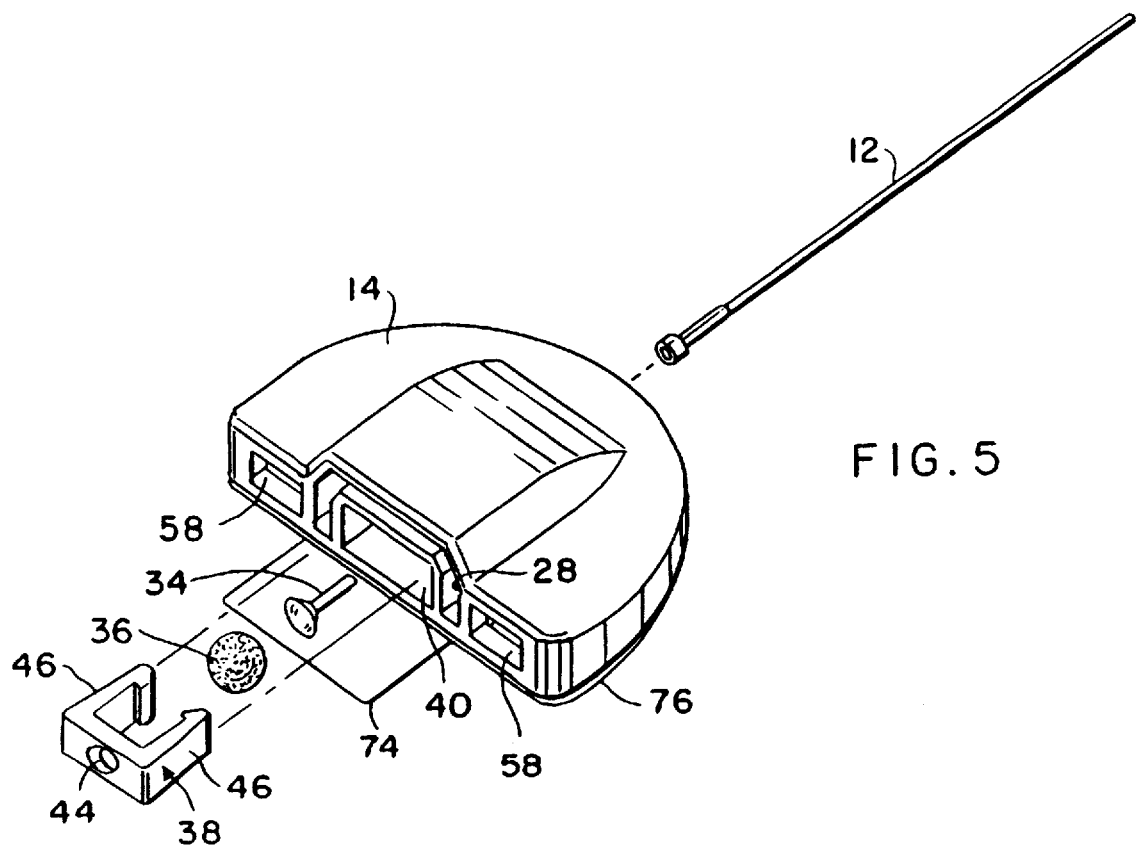
FIG. 5 is an exploded perspective view illustrating assembly of the cannula housing.
Figure 6:
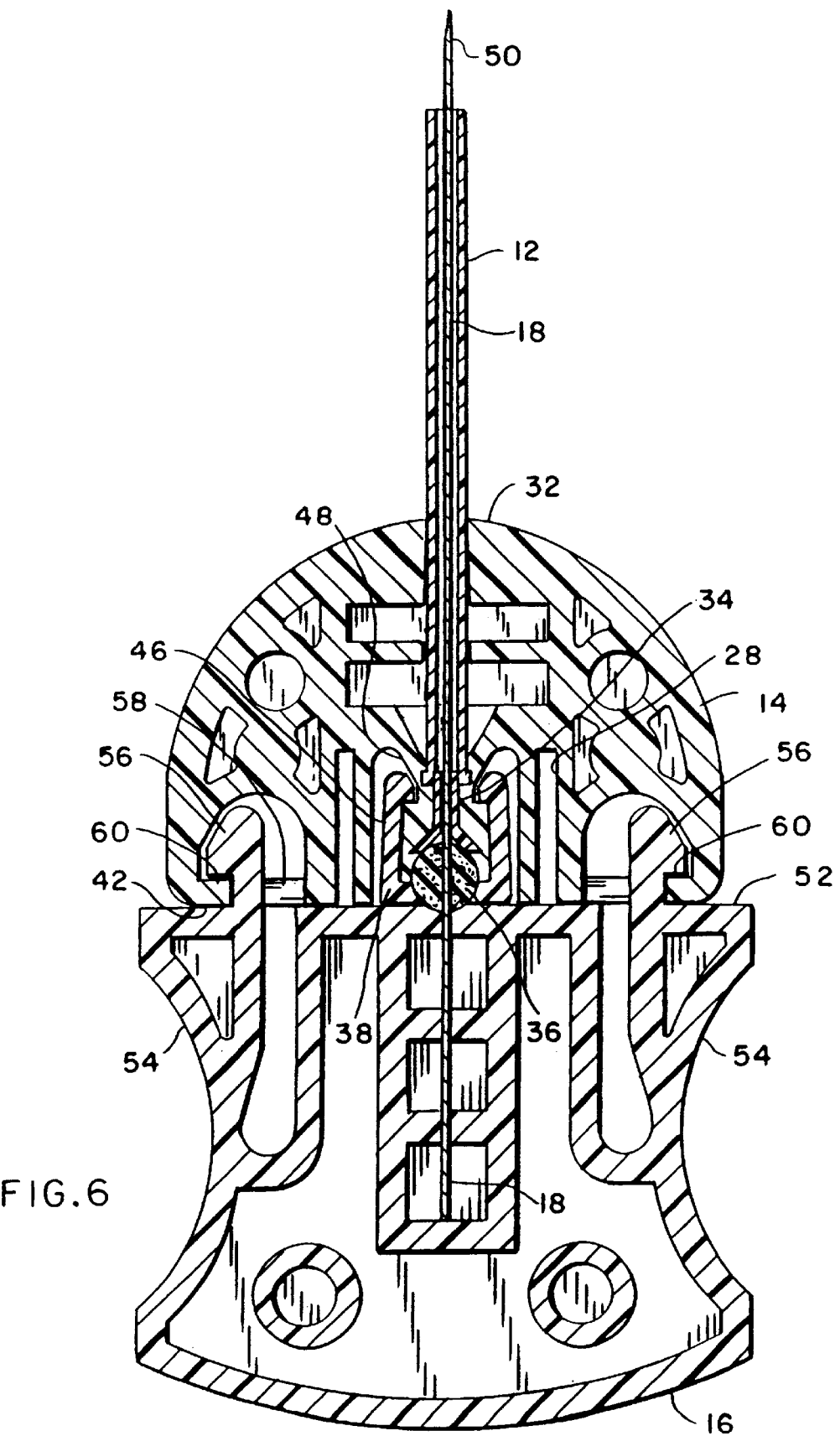
FIG. 6 is a horizontal sectional view showing the cannula housing and insertion hub in assembled relation.
Figure 7:
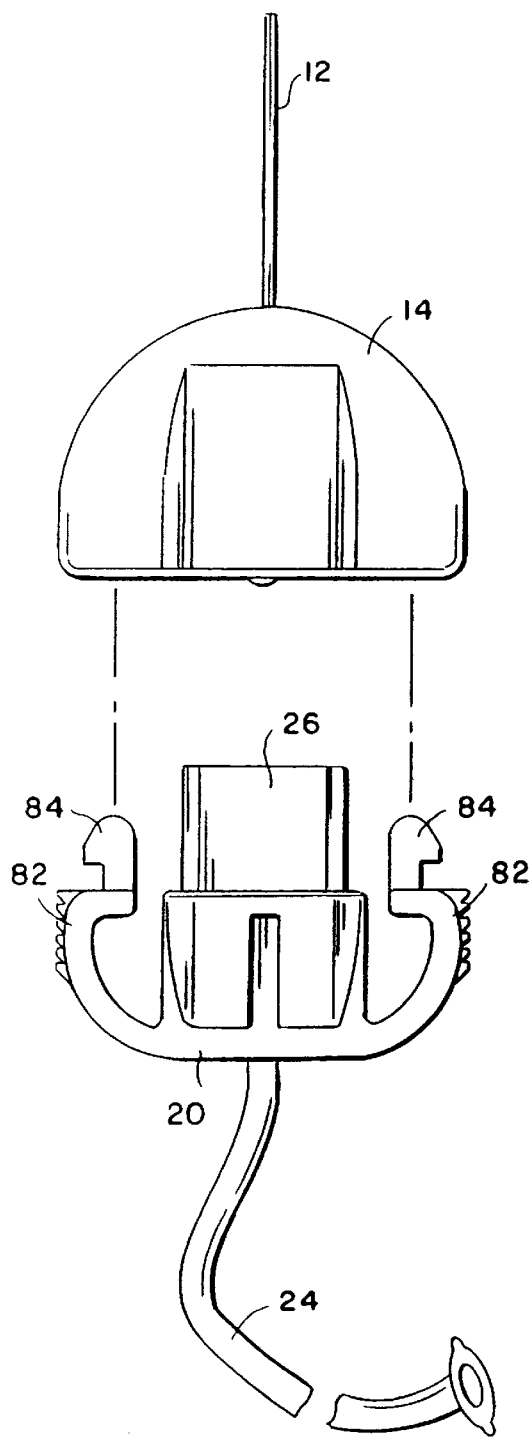
FIG. 7 is a top plan view showing the cannula housing and an infusion hub in exploded relation.
Figure 8:
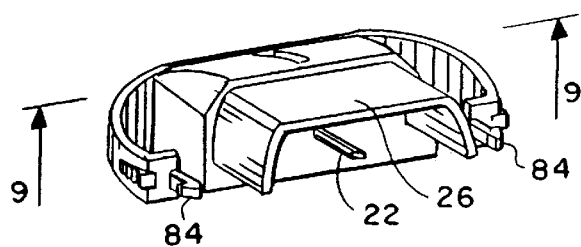
FIG. 8 is a perspective view of the infusion hub shown in FIG. 7, depicting the distal or downstream face thereof.
Figure 9:
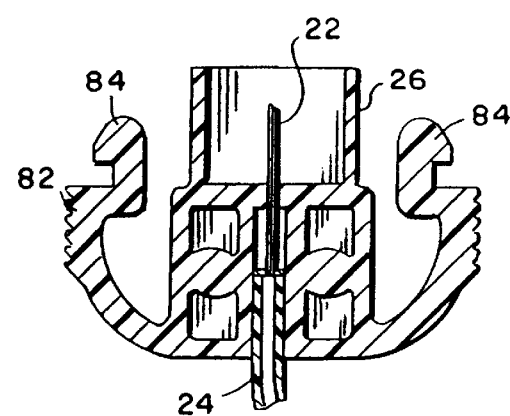
FIG. 9 is a horizontal sectional view of the infusion hub.
Figure 10:
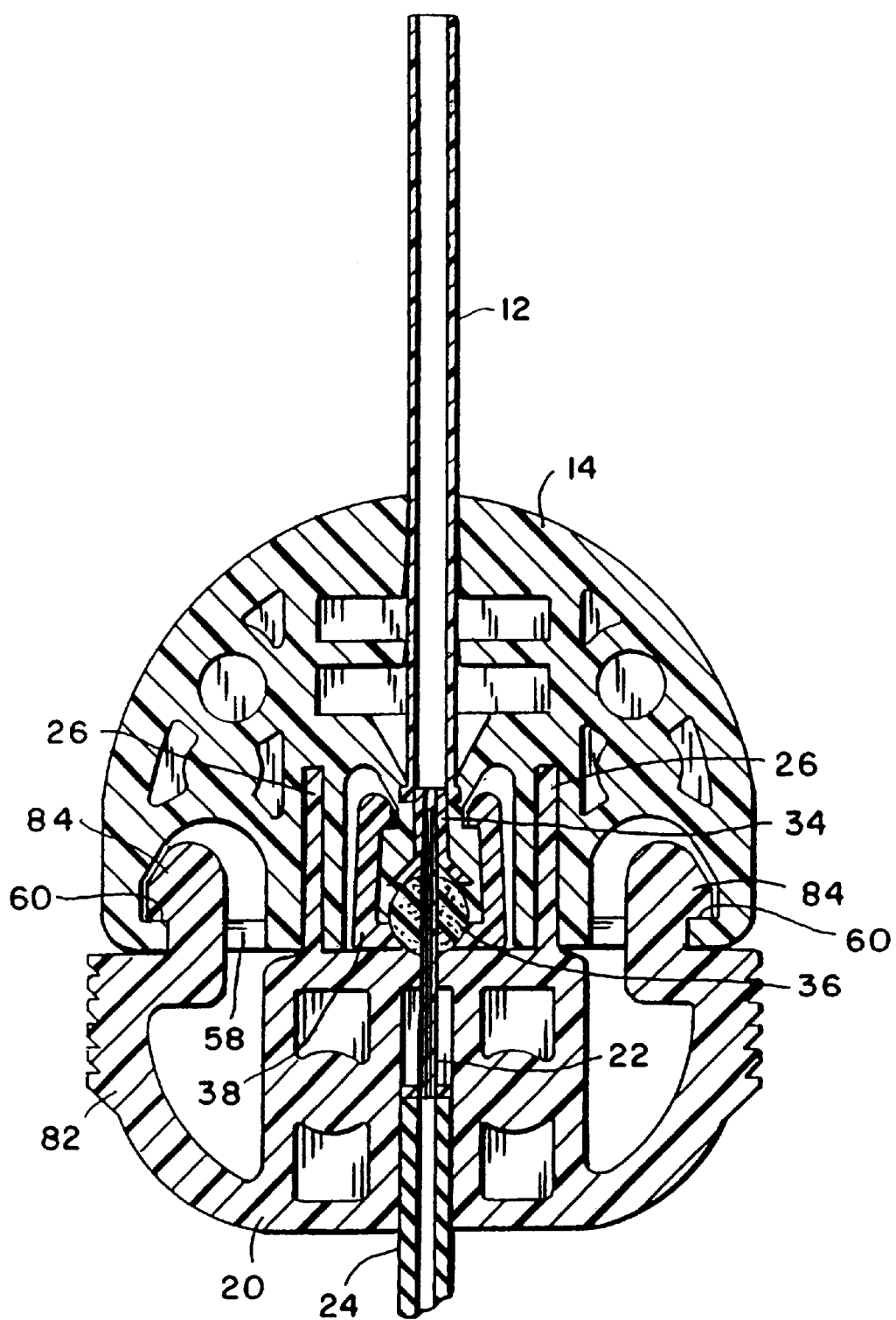
FIG. 10 is a horizontal sectional view showing the cannula housing and infusion hub in assembled relation.

The cannula housing 14 is shown in detail in FIGS. 4–6, to comprise a compact and low profile component constructed from a medical grade molded plastic which is clear or transparent to facilitate viewing of the infusion site. The cannula housing defines a bore 30 extending therethrough and adapted to receive and support an upstream or proximal end of the soft cannula 12, with a distal end of the cannula protruding outwardly from a smoothly rounded distal face 32 of the cannula housing. In the preferred form, the proximal end of the cannula 12 is press-fit mounted onto a downstream end of a needle guide 34 formed from stainless steel or the like, and these assembled components are compression fitted into the bore 30. In this regard, for facilitated assembly, the bore 30 may be formed in the plastic molded cannula housing 14 in the form of a downwardly open channel.

The upstream end of the needle guide 34 is flared outwardly to form a radially enlarged and generally conical seat for receiving and supporting a resilient self-sealing septum 36 in the form of a ball. The septum 36 is securely retained within the flared end of the needle guide 34 by a small generally U-shaped retainer clip 38. This retainer clip 38 is sized and shaped to fit into an open cavity 40 formed in a proximal face 42 of the cannula housing 14, with a centrally located needle port 44 formed in the clip 38 to permit needle access via the septum 36 and needle guide 34 with the cannula 12, as will be described in more detail. The opposing legs of the U-shaped retainer clip 38 include in-turned latch feet 46 for snap-fit engagement into latch detents 48 formed by the cannula housing 14 on opposite sides of the bore 30, to lock the retainer clip 38 onto the cannula housing. The ball-shaped septum conveniently mounts within the flared end of the needle guide in a self-centered manner, and without reference to orientation, to provide a maximized septum surface area and internal volume within a minimum space.

The cannula housing 14 and related cannula 12, as described above, are shown in FIGS. I and 6 in preassembled relation with the insertion hub 16 for use in transcutaneously placing the cannula 12 on the patient at the selected subcutaneous infusion site. To this end, the insertion hub 16 also comprises a compact and low profile component which is preferably formed from molded plastic with an overall size and shape generally conforming with the cannula housing 14. As shown best in FIGS. 2 and 3, the insertion hub 16 rigidly supports a rear or proximal end of the insertion needle 18 which protrudes from the hub 16 and terminates in a pointed distal end tip 50. The insertion needle 18 is adapted to pierce the ball-shaped septum 36 and to extend through the needle guide 34 and further through the soft cannula 12, to position the sharp tip 50 at least slightly beyond the distal end tip of the cannula. In this orientation, a distal face 52 of the insertion hub 16 is substantially butted against the proximal face 42 of the cannula housing 14 (FIGS. 1 and 6). A pair of resilient latch arms 54 on the insertion hub 16 having out-turned latch fingers 56 thereon are received into a corresponding pair of open latch ports 58 formed in the proximal face 42 of the cannula housing, and these latch fingers 56 snap-fit engage with undercut recesses 60 on the cannula housing to retain the insertion hub 16 and the cannula housing 14 in assembled relation.

A shell-shaped needle guard 62 as shown in FIG. 1 is normally provided for mounting onto the preassembled insertion hub 16 and cannula housing 14, to protect against undesired contact with the insertion needle 18. The needle guard 62 may also comprise a simple plastic molding having a size and shape to fit over the protruding insertion needle 16 and the soft cannula 12 thereon, and to include a rearwardly extending clip segment 64 having a latch tooth 66 for releasible reception into an upwardly open notch 68 formed in an upper surface of the insertion hub 16.

Figure 11:
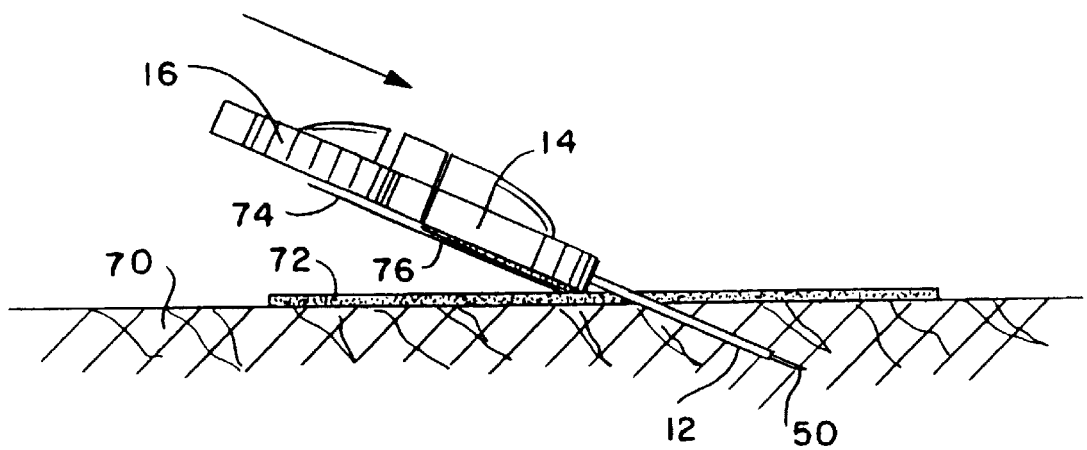
FIG. 11 is a fragmented sectional view illustrating use of the insertion hub for placing the cannula housing on a patient.
Figure 12:
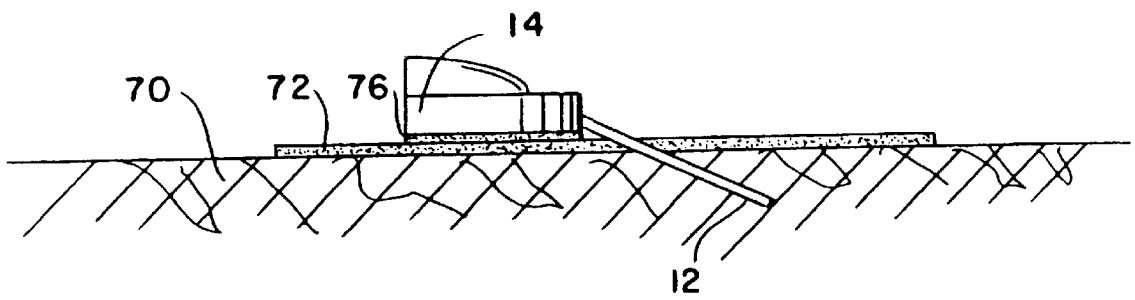
FIG. 12 is a fragmented sectional view similar to FIG. 11, and depicting the cannula housing seated on the patient.

When placement of the cannula 12 on the patient is desired, the needle guard 62 is removed from the preassembled insertion hub and cannula housing to expose the insertion needle 18, as viewed in FIG. 1. The preassembled components are then manipulated as a unit, primarily by grasping the insertion hub 16, to pierce the patient's skin 70 at a selected infusion site as shown in FIG. 11. In this regard, in a preferred placement procedure, the infusion site is prepared by initial cleansing followed by placement of a mounting substrate in the form of a patch 72 mounted onto the skin 70 by means of a suitable hypoallergenic or non-irritating adhesive, such as a patch marketed by Wound Management Division of Smith+Nephew of Largo, Fla. under the product designation OpSite IV 3000. The patch 72 provides a smoother and flatter mounting base of improved lateral stability for more secure mounting of the cannula housing 14, as compared to direct placement onto the patient's skin 70, and has an attachment surface area significantly greater than the underside surface area of the cannula housing. The insertion needle 18 can be inserted transcutaneously by placement directly through the patch 72, typically at an angle to the skin 70 of about 30–45 degrees, to transcutaneously place the cannula 12, with the patch 72 supporting the skin in the region of the needle pierce point. When the cannula is properly placed, the insertion hub 16 can be separated from the cannula housing 14 by squeezing inwardly on the latch arms 54 to permit withdrawal of the insertion needle thereby leaving the cannula 12 in position on the patient. The cannula housing 14 is then secured to the patient by removing a peel-off paper strip 74 from the underside thereof to expose an adhesive layer 76 suited for secure attachment to the patch 72, as viewed in FIG. 12.

In the preferred form, the adhesive layer 76 securing the cannula housing 14 to the patch 72 is chosen for a strong and stable attachment, with the broader and larger surface area of the patch in turn providing a secure and stable mounting relative to the patient's skin 70. As a result, the attachment force retaining the cannula housing 14 to the patch 72, as well as the attachment force retaining the patch 72 to the patient's skin, can significantly exceed the attachment force otherwise achievable by adhering the cannula housing 14 directly to the patient's skin. Accordingly, the cannula housing and the associated cannula 12 are anchored in a manner such that partial pull-out of the cannula is unlikely to occur during normal patient movement and/or inadvertent tugging or pulling of the infusion set. When removal of the cannula is desired, the patch 72 and cannula housing 14 are removed as a unit for disposal. Alternately, it will be understood that the cannula housing 14 may be adhered directly to the patient's skin 70, in the event that the patch 72 is not used.

Following placement of the cannula 12 on the patient, the infusion hub 20 is coupled quickly and easily with the cannula housing 14 for supplying the selected medication to the patient. More particularly, as shown in FIGS. 7–10, the infusion hub 20 also comprises a compact and low profile component of medical grade molded plastic with an overall size and shape for connection to the cannula housing. The infusion hub 20 defines an internal bore 78 for seated reception of the infusion needle 22. A rear end of the infusion needle is positioned for press-fit connection to the length of infusion tubing 24 which, as previously described, is coupled in turn to the appropriate medication source such as a medication infusion pump (not shown). A forward or tip end of the infusion needle 22 protrudes outwardly from a distal face 80 of the infusion hub 20, with a length sufficient to extend through the resilient septum 36 and partially into the metal needle guide 34 within the cannula housing 14, when the infusion hub is connected to the cannula housing. Accordingly, with this geometry, the infusion needle 22 does not protrude beyond the needle guide 34 into the soft cannula 12, thereby minimizing or eliminating risk of needle-caused damage to the soft cannula. A pair of resilient latch arms 82 also project from the distal face 80 of the infusion hub 20 and include out-turned latch fingers 84 for snap-fit engagement into the latch recesses 60 formed in the cannula housing 14 to releasibly lock the components together, with the infusion needle 22 coupling the infusion tubing 24 with the cannula 12.

In accordance with one primary aspect of the invention, the shroud plate 26 extends from the distal face of the infusion hub 20 to closely overlie and protect the infusion needle. As shown, the shroud plate 26 comprises a multi-faceted and preferably three-sided structure extending over the top and both sides of the infusion needle 22, and projecting from the infusion hub at least slightly beyond the distal end tip of the infusion needle. With this construction, the shroud plate substantially and effectively shields the infusion needle 22 against significant risk of patient contact therewith during manipulation of the infusion hub to connect or disconnect the infusion tubing from the cannula, thereby substantially preventing undesirable needle sticks.

Moreover, the protective shroud plate 26 presents a keyed structure for unidirectional or one-way connection of the infusion hub 20 with the cannula housing 14, in a manner providing a strong interconnection with accurate guided coupling of the infusion needle 22 through the septum 36 and into the needle guide 34, yet additionally permitting quick and easy disconnection when desired. Specifically, the shroud plate 26 is sized and shaped for slide-fit reception into the matingly shaped and thus preferably three-sided slot 28 formed in the proximal face 42 of the cannula housing 14, to extend over the top and at both sides of the retainer clip 38. The shroud plate 26 slidably fits into the slot 28 in one orientation only, thereby properly positioning and aligning the infusion needle 22 with the retainer clip port 44. As the shroud plate 26 is advanced into the mating slot 28, the needle 22 correspondingly advances through the septum and partially into the needle guide 34, while the latch arms 82 advance into the latch ports 58 for snap-fit connection of the infusion hub 20 to the cannula housing 14. When fully connected, the shroud plate 26 presents a broad and multi-faceted surface area engaging the cannula housing within the slot 28 to provide a strong interconnection which is highly resistant to bending, twisting and other forces otherwise contributing to potential inadvertent separation of the components.

However, when disconnection of the components is desired, the latch arms 82 are quickly and easily pressed inwardly to release from the associated latch recesses 60, to permit simple slide-apart separation of the infusion hub 20 from the cannula housing 14. The shroud plate 26 presents a central housing structure between the latch arms 82 to block excess displacement when the latch arms are pressed inwardly, thereby protecting the latch arms against permanent deformation and/or breakage, and correspondingly permitting repeated connection and disconnection of the infusion hub. Importantly, upon such separation, the septum 36 seals the upstream end of the cannula to maintain sterility. During this separated condition, the patient may participate in a variety of activities such as athletic events, swimming or bathing, wherein it may be desirable to avoid exposure of the medication source such as an infusion pump to physical jarring or to water, etc. Alternately, with the infusion hub 20 separated from the cannula housing 14, other medications can be administered to the patient by means of a syringe or the like piercing the septum 36. Still further, separation of the infusion hub 20 from the cannula housing 14 is typically desired at intervals of a few days to permit removal of an in situ cannula and replacement with a new one. In all cases, the infusion hub 20 is quickly and easily reconnected to the associated cannula housing 14 with a simple sliding and snap-fit one-way attachment.

A variety of further modifications and improvements in and to the improved medication infusion set of the present invention will be apparent to persons skilled in the art. Accordingly, no limitation on the invention is intended by way of the foregoing description and accompanying drawings, except at set forth in the appended claims.

What is claimed is:

1. A medication infusion set for delivery of a selected medication to a patient, the infusion set comprising:
    a cannula housing having a soft cannula mounted thereon with a distal end of the cannula protruding from the cannula housing, wherein a shaped portion of the cannula housing surrounds a resilient self-sealing septum mounted on the cannula housing generally for normally closing a proximal end of the cannula; and
    an infusion hub includes tubing being adapted for connection to a source of the selected medication, wherein the infusion hub includes an infusion needle mounted thereon with a distal end of the infusion needle protruding from the infusion hub, and wherein the infusion needle is adapted for insertion through the septum in the shaped portion of the cannula housing for coupling with the cannula,
    wherein the infusion hub further includes a protective shroud protruding therefrom in overlying relation with the infusion needle to reduce inadvertent contact of the infusion needle with a patient, wherein the shroud being a guide to slidably cover the generally matingly shaped portion of the cannula housing for guided reception of the infusion needle through the septum mounted in the shaped portion of the cannula housing, and wherein an exterior of the shroud comprises a plurality of generally planar facets, and
    wherein the cannula housing and the infusion hub further includes releasibly interengageable latch members for releasibly connecting the infusion hub to the cannula housing with the infusion needle inserted through said septum.

2. The medication infusion set of claim 1, wherein the shroud on the infusion hub surrounds at least three sides of the infusion needle.

3. The medication infusion set of claim 1, wherein the shroud on the infusion hub provides unidirectional alignment of the infusion hub with the cannula housing.

4. The medication infusion set of claim 1, further including a rigid tubular needle guide interposed between the septum and the proximal end of the cannula.

5. The medication infusion set of claim 4, wherein the infusion needle has a length to extend through the septum and partially into the needle guide when the cannula housing and infusion hub are connected together.

6. The medication infusion set of claim 1, wherein the septum comprises a resilient self-sealing ball.

7. The medication infusion set of claim 1, wherein the shroud extends over at least the top and opposite sides of the infusion needle.

8. The medication infusion set of claim 1, wherein the shroud extends from the infusion hub at least slightly beyond a distal end of the infusion needle.

9. The medication infusion set of claim 1, wherein the latch members comprise at least one resilient latch arm protruding from the infusion hub and at least one latch port having a latch detent therein formed on the cannula housing for snap-fit and releasible engagement with the latch arm.

10. The medication infusion set of claim 1, wherein the latch members comprises a pair of resilient latch arms protruding from the infusion hub at opposite sides of the shroud, and a corresponding pair of latch ports each having a latch detent therein formed on the cannula housing for snap-fit and releasible engagement with the latch arms.

11. The medication infusion set of claim 1, further including an adhesive layer on an underside surface of the cannula housing.

12. A medication infusion set for delivery of a selected medication to a patient, the infusion set comprising:

a cannula housing having a soft cannula mounted thereon with a distal end of the cannula protruding from the cannula housing, wherein a shaped portion of the cannula housing surrounds a resilient self-sealing septum mounted on the cannula housing generally for normally closing a proximal end of the cannula; and an infusion hub includes tubing being adapted for connection to a source of the selected medication, wherein the infusion hub includes an infusion needle mounted thereon with a distal end of the infusion needle protruding from the infusion hub, and wherein the infusion needle is adapted for insertion through the septum in the shaped portion of the cannula housing for coupling with the cannula, wherein the infusion hub further includes a protective shroud protruding therefrom in overlying relation with the infusion needle to reduce inadvertent contact of the infusion needle with a patient, wherein the shroud being a guide to slidably cover the generally matingly shaped portion of the cannula housing for guided reception of the infusion needle through the septum mounted in the shaped portion of the cannula housing, and wherein the shroud on the infusion hub surrounds three sides of the infusion needle, and wherein the cannula housing and the infusion hub further includes releasibly interengageable latch members for releasibly connecting the infusion hub to the cannula housing with the infusion needle inserted through said septum.

13. A medication infusion set for delivery of a selected medication to a patient, the infusion set comprising:

a cannula housing having a soft cannula mounted thereon with a distal end of the cannula protruding from the cannula housing, wherein a shaped portion of the cannula housing surrounds a resilient self-sealing septum mounted on the cannula housing generally for normally closing a proximal end of the cannula; and an infusion hub includes tubing being adapted for connection to a source of the selected medication, wherein the infusion hub includes an infusion needle mounted thereon with a distal end of the infusion needle protruding from the infusion hub, and wherein the infusion needle is adapted for insertion through the septum in the shaped portion of the cannula housing for coupling with the cannula, wherein the infusion hub further includes a protective shroud protruding therefrom in overlying relation with the infusion needle to reduce inadvertent contact of the infusion needle with a patient, wherein the shroud being a guide to slidably cover the generally matingly shaped portion of the cannula housing for guided reception of the infusion needle through the septum mounted in the shaped portion of the cannula housing, and wherein the shroud on the infusion hub fits in a slot formed in the cannula housing, and wherein the cannula housing and the infusion hub further includes releasibly interengageable latch members for releasibly connecting the infusion hub to the cannula housing with the infusion needle inserted through said septum.

* * * * *